United States Patent
Tomizawa et al.

(10) Patent No.: US 12,214,095 B2
(45) Date of Patent: Feb. 4, 2025

(54) DISINFECTION DEVICE AND DISINFECTION SYSTEM

(71) Applicant: TOYOTA JIDOSHA KABUSHIKI KAISHA, Toyota (JP)

(72) Inventors: Ryota Tomizawa, Susono (JP); Shozo Takaba, Chiryu (JP); Ayako Shimizu, Numazu (JP); Hojung Jung, Sunto-gun Shizuoka-ken (JP); Daisuke Sato, Toyota (JP); Yasuhiro Kobatake, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 361 days.

(21) Appl. No.: 17/870,122

(22) Filed: Jul. 21, 2022

(65) Prior Publication Data

US 2023/0053825 A1  Feb. 23, 2023

(30) Foreign Application Priority Data

Aug. 23, 2021  (JP) .................... 2021-135645

(51) Int. Cl.
  *A61L 2/10*  (2006.01)
(52) U.S. Cl.
  CPC ............ *A61L 2/10* (2013.01); *A61L 2202/11* (2013.01); *A61L 2202/14* (2013.01); *A61L 2202/25* (2013.01)

(58) Field of Classification Search
  CPC ..... A61L 2/10; A61L 2/24; A61L 2/26; A61L 2202/11; A61L 2202/14; A61L 2202/25
  See application file for complete search history.

(56) References Cited

U.S. PATENT DOCUMENTS

| | | | |
|---|---|---|---|
| 2017/0049915 A1 | 2/2017 | Brais et al. | |
| 2021/0015959 A1 | 1/2021 | Goseki et al. | |
| 2021/0308311 A1* | 10/2021 | Stewart | A61L 2/10 |
| 2022/0088249 A1* | 3/2022 | Kyle | B60Q 3/68 |

FOREIGN PATENT DOCUMENTS

| | | |
|---|---|---|
| JP | 2001-321430 A | 11/2001 |
| JP | 2005-213959 A | 8/2005 |
| JP | 2017-029293 A | 2/2017 |
| JP | 2017-528258 A | 9/2017 |
| JP | 2019-536492 A | 12/2019 |
| JP | 3229192 U | 12/2020 |
| WO | 2016/049143 A2 | 3/2016 |
| WO | 2018/041986 A1 | 3/2018 |
| WO | 2019/186880 A1 | 10/2019 |

* cited by examiner

*Primary Examiner* — David E Smith
*Assistant Examiner* — Hsien C Tsai
(74) *Attorney, Agent, or Firm* — Dinsmore & Shohl LLP

(57) ABSTRACT

A disinfection system disinfects an inside of a building or a moving body. The disinfection system includes an ultraviolet irradiator, a recognition sensor that recognizes a situation of the inside of the building or the moving body, and a control device configured to automatically control the ultraviolet irradiator based on the situation of the inside of the building or the moving body, which is recognized by the recognition sensor, to disinfect the inside of the building or the moving body.

8 Claims, 2 Drawing Sheets

DISINFECTION DEVICE AND DISINFECTION SYSTEM

CROSS-REFERENCE TO RELATED APPLICATION

This application claims priority to Japanese Patent Application No. 2021-135645 filed on Aug. 23, 2021, incorporated herein by reference in its entirety.

BACKGROUND

1. Technical Field

The present disclosure relates to a disinfection device and a disinfection system.

2. Description of Related Art

Japanese Unexamined Patent Application Publication No. 2005-213959 discloses a handrail disclosed in the related art in which a deodorant is filled inside the handrail in order to add a deodorizing function and an air purifying function to the handrail.

SUMMARY

The above-described handrail disclosed in the related art deodorizes and purifies the air around the handrail, and does not disinfect a part touched by a person such as a grip part (surface) of the handrail. As a method of disinfecting a part touched by a person, for example, a method of spraying a disinfectant solution on a part touched by a person can be considered. However, this method may not spray the parts (that is, the disinfected parts) evenly and it may take time for the sprayed disinfectant solution to dry.

The present disclosure provides a disinfection device and a disinfection system that disinfect a part touched by a person.

According to an aspect of the present disclosure, a disinfection system that disinfects an inside of a building or a moving body includes an ultraviolet irradiator, a recognition sensor that recognizes a situation of the inside of the building or the moving body, and a control device configured to automatically control the ultraviolet irradiator based on the situation of the inside of the building or the moving body, which is recognized by the recognition sensor, to disinfect the inside of the building or the moving body.

With an aspect of the present disclosure, it is possible to appropriately disinfect a part touched by a person by ultraviolet rays.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

Hereinafter, an embodiment of the present disclosure will be described in detail with reference to the drawings. In the following description, similar components are given the same reference numbers. In the present specification, the term "disinfection" includes not only detoxifying bacteria and viruses but also reducing the presence of (sterilizing) bacteria and viruses.

Figure 1:
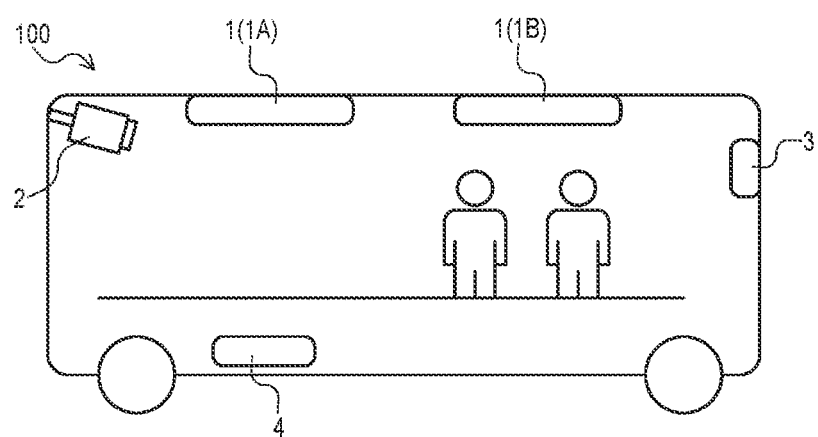
FIG. 1 is a schematic configuration diagram of a disinfection system according to an embodiment of the present disclosure.

FIG. 1 is a schematic configuration diagram of a disinfection system 100 according to an embodiment of the present disclosure. Although FIG. 1 illustrates the disinfection system 100 for disinfecting the inside of a bus, it is also possible to disinfect the inside of a vehicle (moving body) other than a bus or the inside of a building by the same configuration.

The disinfection system 100 includes an ultraviolet irradiator 1, a recognition sensor 2, an alarm device 3, and a control device 4.

The ultraviolet irradiator 1 irradiates a passenger compartment of the bus with ultraviolet rays to disinfect an irradiation target object. The switching on and off of the ultraviolet irradiator 1 is controlled by the control device 4. An example of the irradiation target object includes a body support that can be gripped by a hand such as a handrail or a hanging strap installed in the passenger compartment of a bus for the purpose of supporting a body or assisting walking. Further, examples of the irradiation target object include walls, windows, seats, and the like that may be touched by hands.

In the present embodiment, as illustrated in FIG. 1, ultraviolet irradiators 1A, 1B are respectively installed in the front and rear of the passenger compartment of the bus such that the front and rear of the passenger compartment of the bus can be individually irradiated. The mounting location and the number of ultraviolet irradiators 1 are not particularly limited. The ultraviolet irradiator 1 may be appropriately set such that a part to be disinfected is included in an irradiation range. The ultraviolet irradiator 1 may be provided with directivity such that a desired irradiation range can be irradiated by changing the irradiation range of the ultraviolet irradiator 1. Further, by reflecting the ultraviolet rays using a mirror or the like, a part that cannot be directly irradiated by the ultraviolet irradiator 1 may be irradiated.

The recognition sensor 2 is a sensor for recognizing the situation in the inside of the passenger compartment of the bus, more specifically, a sensor for recognizing whether there are passengers in the passenger compartment of the bus, and when there are passengers in the passenger compartment of the bus, in which part (for example, the front and rear of the passenger compartment, and the like) of the passenger compartment the passengers are present. In the present embodiment, as the recognition sensor 2, a camera installed in a place where the entire passenger compartment of the bus can be seen is used, but the installation location and the number of installations are not limited thereto. Further, another sensor (for example, a motion sensor, or the like) can be used as the recognition sensor 2. The camera as the recognition sensor 2 periodically photographs the passenger compartment of the bus and transmits the captured image to the control device 4.

The alarm device 3 is a device for giving various warnings and notifications to bus passengers using light, sound, an image, or the like. The alarm device 3 is controlled by the control device 4.

The control device 4 is, for example, a general-purpose computer equipped with a communication function, and includes a central processing unit (CPU), a memory such as a read-only memory (ROM) and a random access memory (RAM), an input port, an output port, and the like which are connected to one another by a bidirectional bus. The control device 4 controls the ultraviolet irradiator 1 and the alarm device 3 based on the situation in the inside of the passenger compartment of the bus.

In the present embodiment, the control device 4 determines whether there are passengers in the passenger compartment of the bus by performing image processing on the images taken by the camera, and when there are passengers in the passenger compartment of the bus, determines in which part (for example, the front and rear of the passenger compartment, and the like) of the passenger compartment the passengers are present. Then, based on the determination result, the control device 4 controls the ultraviolet irradiator 1 to irradiate the passenger compartment of the bus with ultraviolet rays, and controls the alarm device 3 as necessary to warn the passengers of the bus that ultraviolet disinfection will be carried out.

Figure 2:
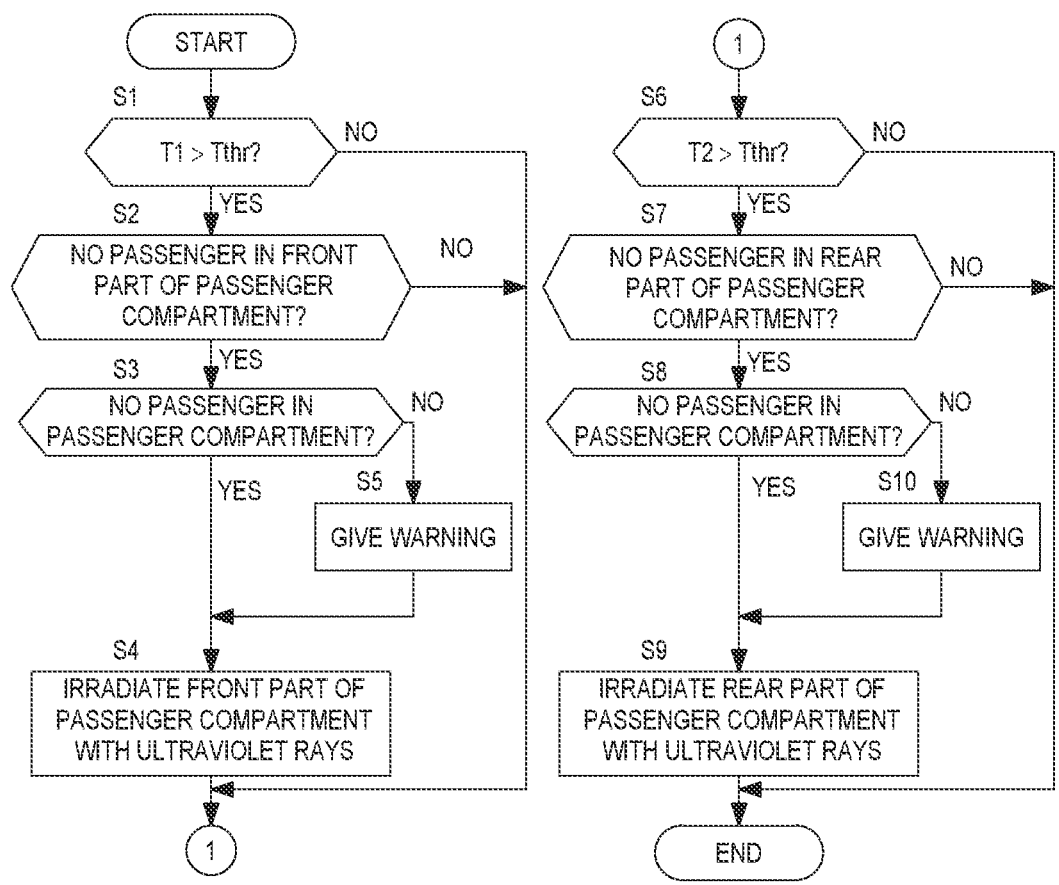
FIG. 2 is a flowchart illustrating an example of a process for controlling an ultraviolet irradiator.

FIG. 2 is a flowchart illustrating an example of a process executed by the control device 4 in order to control the ultraviolet irradiator 1.

In step S1, the control device 4 determines whether an elapsed time T1 since the previous irradiation on the front part of the passenger compartment is equal to or longer than a preset predetermined time Tthr. When the elapsed time T1 is equal to or longer than the predetermined time Tthr, the control device 4 proceeds to the process of step S2. On the other hand, when the elapsed time T1 is less than the predetermined time Tthr, the control device 4 proceeds to the process of step S6.

In step S2, the control device 4 determines, based on the images taken by the camera, whether there is a passenger within an irradiation range of the ultraviolet irradiator 1A that irradiates the front part of the passenger compartment. The control device 4 proceeds to the process of step S3 when there is no passenger who exists in the irradiation range of the ultraviolet irradiator 1A, that is, in the front part of the passenger compartment. On the other hand, when there is a passenger in the front part of the passenger compartment, the control device 4 proceeds to the process of step S6.

In step S3, the control device 4 determines, based on the images taken by the camera, whether there is a passenger in the passenger compartment. The control device 4 proceeds to the process of step S4 when there is no passenger in the passenger compartment. On the other hand, the control device 4 proceeds to the process of step S5 when there is even one passenger in the passenger compartment.

In step S4, the control device 4 automatically disinfects the front part of the passenger compartment by irradiating the front part of the passenger compartment with ultraviolet rays by the ultraviolet irradiator 1A. Further, the control device 4 returns the elapsed time T1 to zero and counts again.

In step S5, the control device 4 controls the alarm device 3 to warn the passengers in the rear part of the passenger compartment that ultraviolet disinfection will be carried out on the front part of the passenger compartment. The warning method is not particularly limited. A warning may be made by causing a light to blink, a warning may be given by sound or voice, a warning may be given by displaying a warning message on a screen, or these may be combined and executed in sequence or at the same time.

In step S6, the control device 4 determines whether an elapsed time T2 since the previous irradiation on the rear part of the passenger compartment is equal to or longer than the preset predetermined time Tthr. When the elapsed time T2 is equal to or longer than the predetermined time Tthr, the control device 4 proceeds to the process of step S7. On the other hand, when the elapsed time T2 is less than the predetermined time Tthr, the control device 4 ends this process without disinfecting the passenger compartment.

In step S7, the control device 4 determines, based on the images taken by the camera, whether there is a passenger within an irradiation range of the ultraviolet irradiator 1B that irradiates the rear part of the passenger compartment. The control device 4 proceeds to the process of step S8 when there is no passenger within the irradiation range of the ultraviolet irradiator 1B, that is, in the rear part of the passenger compartment. On the other hand, when there is a passenger in the rear part of the passenger compartment, the control device 4 ends this process without disinfecting the passenger compartment.

In step S8, the control device 4 determines, based on the images taken by the camera, whether there is a passenger within the passenger compartment. The control device 4 proceeds to the process of step S9 when there is no passenger within the passenger compartment. On the other hand, the control device 4 proceeds to the process of step S10 when there is even one passenger within the passenger compartment.

In step S9, the control device 4 automatically disinfects the rear part of the passenger compartment by irradiating the rear part of the passenger compartment with ultraviolet rays by the ultraviolet irradiator 1B. Further, the control device 4 returns the elapsed time T2 to zero and counts again.

In step S10, the control device 4 controls the alarm device 3 to warn the passengers in the front part of the passenger compartment that ultraviolet disinfection will be carried out on the rear part of the passenger compartment.

The disinfection system 100 according to the present embodiment described above is a disinfection system that disinfects the passenger compartment (inside a building or a moving body) of a bus. The disinfection system 100 includes the ultraviolet irradiator 1, the recognition sensor 2 that recognizes the situation in the passenger compartment of the bus, and the control device 4 configured to automatically control the ultraviolet irradiator 1 based on the situation in the passenger compartment of the bus, which is recognized by the recognition sensor 2, to disinfect the passenger compartment of the bus.

As a result, the part of the building or moving body that is touched by a person can be automatically disinfected by ultraviolet rays. In addition, unlike the case of disinfecting by spraying a disinfectant solution, the parts irradiated with ultraviolet rays can be evenly disinfected, and the disinfectant solution does not adhere to the parts even when the irradiated parts are touched immediately after irradiation, such that the parts touched by a person can be appropriately disinfected.

In the present embodiment, the control device 4 is configured to perform irradiation by the ultraviolet irradiator 1 when it is determined, based on a recognition result by the recognition sensor 2, that there is no person within the irradiation range of the ultraviolet irradiator 1. Further, the control device 4 is configured not to perform irradiation by the ultraviolet irradiator 1 when it is determined that there is a person within the irradiation range of the ultraviolet irradiator 1.

As a result, it is possible to prevent the passengers from being irradiated with ultraviolet rays.

In particular, in the present embodiment, the control device 4 is configured to, when it is determined, based on a recognition result by the recognition sensor 2, that there is no person within an irradiation range of the ultraviolet irradiator 1 but there is a person who exists outside the irradiation range, perform irradiation by the ultraviolet irradiator 1 after giving a warning to a person who exists outside the irradiation range.

As a result, it is possible to prevent the passengers from being irradiated with ultraviolet rays while increasing the frequency of irradiation (frequency of disinfection) with ultraviolet rays.

Although the embodiment of the present disclosure is described above, the embodiment described above is only a part of the application examples of the present disclosure, and the technical scope of the present disclosure is not intended to be limited to the specific configuration of the embodiment described above.

For example, in the embodiment described above, the warning given in steps S5 and S10 of FIG. 2 is given by the alarm device 3, but the warning is not limited thereto. Communication may be performed between a terminal and the control device such that the terminal (for example, a smartphone or the like) owned by the passenger gives a warning.

Further, for example, in the embodiment described above, when performing ultraviolet disinfection in the passenger compartment of a bus after giving a warning in steps S5 or S10 of FIG. 2, for example, along with the warning, a shielding object that physically blocks ultraviolet rays, such as a shielding curtain installed between the front part and the rear part of the passenger compartment of the bus, may be automatically operated, and ultraviolet disinfection may then be performed in the passenger compartment of the bus after physically blocking the part between the front part and the rear part of the passenger compartment of the bus.

In addition, in order to inform passengers who are about to board the bus that the bus has just been disinfected with ultraviolet rays, for a certain period of time after the ultraviolet disinfection, the alarm device 3 may be used to inform passengers of this, or a notification indicating that the fact may be sent to a terminal of a newly boarded passenger.

What is claimed is:

1. A disinfection system that disinfects an inside of a vehicle, the disinfection system comprising:
   a plurality of ultraviolet irradiators including a first ultraviolet irradiator positioned at a front portion of a passenger compartment of the vehicle and a second ultraviolet irradiator positioned at a rear portion of the passenger compartment of the vehicle;
   a recognition sensor that recognizes a situation of the inside of the vehicle, the recognition sensor including a camera; and
   a control device configured to automatically control the plurality of ultraviolet irradiators based on the situation of the inside of the vehicle, which is recognized by the recognition sensor, to disinfect the inside of the vehicle, wherein:
   the control device is configured to selectively switch on and off the plurality of ultraviolet irradiators, and
   the control device is configured to determine a first elapsed time since a previous irradiation by the first ultraviolet irradiator at the front portion relative to a first threshold time, and a second elapsed time since another previous irradiation by the second ultraviolet irradiator at the rear portion relative to the first threshold time.

2. The disinfection system according to claim 1, wherein the control device is configured to, upon determining, based on a recognition result by the recognition sensor, that there is no person within an irradiation range of the plurality of ultraviolet irradiators, perform irradiation by the plurality of ultraviolet irradiators.

3. The disinfection system according to claim 1, wherein the control device is configured to, upon determining, based on a recognition result by the recognition sensor, that there is no person within an irradiation range of the plurality of ultraviolet irradiators but there is a person who exists outside the irradiation range, perform irradiation by the plurality of ultraviolet irradiators after giving a warning to the person who exists outside the irradiation range.

4. The disinfection system according to claim 1, wherein the control device is configured, upon determining, based on a recognition result by the recognition sensor, that there is a person within an irradiation range of the plurality of ultraviolet irradiators, not to perform irradiation by the plurality of ultraviolet irradiators.

5. The disinfection system according to claim 1, further comprising an alarm device configured to output one or more notifications using light, a sound, an image, or any combination thereof in a predetermined manner, including sequentially or simultaneously.

6. The disinfection system according to claim 1, wherein the camera is configured to periodically capture one or more images and transmit the one or more images to the control device.

7. The disinfection system according to claim 1, wherein control device configured to reset the first elapsed time to zero and count again after disinfecting one of the front portion or the rear portion of the passenger compartment.

8. The disinfection system according to claim 1, wherein the inside of the vehicle includes an irradiation target object that comprises a handrail or a hanging strap.

* * * * *